(12) United States Patent
Santini, Jr. et al.

(10) Patent No.: US 6,976,982 B2
(45) Date of Patent: Dec. 20, 2005

(54) FLEXIBLE MICROCHIP DEVICES FOR OPHTHALMIC AND OTHER APPLICATIONS

(75) Inventors: John T. Santini, Jr., Belmont, MA (US); Michael J. Cima, Winchester, MA (US); Robert S. Langer, Newton, MA (US); Dennis Ausiello, Wellsley Hill, MA (US); Norman F. Sheppard, Jr., Bedford, MA (US); Stephen J. Herman, Andover, MA (US)

(73) Assignee: MicroCHIPS, Inc., Bedford, MA (US)

(*) Notice: Subject to any disclaimer, the term of this patent is extended or adjusted under 35 U.S.C. 154(b) by 574 days.

(21) Appl. No.: 10/042,996

(22) Filed: Jan. 9, 2002

(65) Prior Publication Data

US 2002/0099359 A1   Jul. 25, 2002

Related U.S. Application Data

(60) Provisional application No. 60/260,725, filed on Jan. 9, 2001.

(51) Int. Cl.[7] .................. A61K 9/22; A61M 31/00; A61B 5/05
(52) U.S. Cl. ............... 604/891.1; 604/66; 600/365
(58) Field of Search .................. 604/65, 66, 131, 604/890.1, 891.1; 600/347, 348, 365

(56) References Cited

U.S. PATENT DOCUMENTS

| | | |
|---|---|---|
| 3,692,027 A | 9/1972 | Ellinwood, Jr. |
| 4,360,019 A | 11/1982 | Portner et al. |
| 4,507,115 A | 3/1985 | Kambara et al. |
| 4,585,652 A | 4/1986 | Miller et al. |
| 4,731,049 A | 3/1988 | Parsi |
| 4,793,825 A | 12/1988 | Benjamin et al. |
| 5,042,975 A | 8/1991 | Chien et al. |
| 5,167,625 A | 12/1992 | Jacobsen et al. |
| 5,170,801 A | 12/1992 | Casper et al. |
| 5,200,051 A | 4/1993 | Cozzette et al. |
| 5,252,294 A | 10/1993 | Kroy et al. |
| 5,279,607 A | 1/1994 | Schentag et al. |
| 5,318,557 A | 6/1994 | Gross |
| 5,324,316 A | 6/1994 | Schulman et al. |

(Continued)

FOREIGN PATENT DOCUMENTS

DE   197 16 683   6/1998

(Continued)

OTHER PUBLICATIONS

Ambati, et al., "Transscleral Delivery of Antibodies to the Posterior Segment," Investigative Ophthalm. & Visual Sci., 40(4):457-B417 (1999).

(Continued)

*Primary Examiner*—Nicholas D. Lucchesi
*Assistant Examiner*—Mark K. Han
(74) *Attorney, Agent, or Firm*—Sutherland Asbill & Brennan LLP (57) ABSTRACT

Microchip device arrays that can conform to a curved surface are provided for the controlled release or exposure of reservoir contents. The arrays comprise two or more microchip device elements, each of which includes a plurality of reservoirs that contain molecules for controlled release or components for selective exposure, and a means for flexibly connecting the device elements. The reservoirs can contain one or more drugs and/or one or more secondary devices, such as a sensor or a component thereof. Preferably, the microchip devices contain and controllably release therapeutic, prophylactic, and diagnostic molecules to and into the eye of a patient in need thereof.

24 Claims, 3 Drawing Sheets

U.S. PATENT DOCUMENTS

| | | | |
|---|---|---|---|
| 5,336,213 | A | 8/1994 | D'Angelo et al. |
| 5,366,454 | A | 11/1994 | Currie et al. |
| 5,368,588 | A | 11/1994 | Bettinger |
| 5,368,704 | A | 11/1994 | Madou et al. |
| 5,429,822 | A | 7/1995 | Gresser et al. |
| 5,443,508 | A | 8/1995 | Giampapa |
| 5,474,527 | A | 12/1995 | Bettinger |
| 5,585,069 | A | 12/1996 | Zanzucchi et al. |
| 5,707,643 | A | 1/1998 | Ogura et al. |
| 5,713,954 | A | 2/1998 | Rosenberg et al. |
| 5,743,274 | A | 4/1998 | Peyman |
| 5,797,898 | A | 8/1998 | Santini, Jr. et al. |
| 5,798,042 | A | 8/1998 | Chu et al. |
| 5,807,397 | A | 9/1998 | Barreras |
| 5,824,072 | A | 10/1998 | Wong |
| 5,841,122 | A | 11/1998 | Kirchhoff |
| 5,842,787 | A | 12/1998 | Kopf-Sill et al. |
| 5,843,767 | A | 12/1998 | Beattie |
| 5,962,081 | A | 10/1999 | Öhman et al. |
| 5,976,336 | A | 11/1999 | Dubrow et al. |
| 5,989,445 | A | 11/1999 | Wise et al. |
| 6,047,214 | A | 4/2000 | Mueller et al. |
| 6,063,116 | A | 5/2000 | Kelleher et al. |
| 6,071,819 | A * | 6/2000 | Tai et al. .................... 438/694 |
| 6,096,656 | A | 8/2000 | Matzke et al. |
| 6,123,861 | A | 9/2000 | Santini, Jr. et al. |
| 6,124,259 | A | 9/2000 | Delmage et al. |
| 6,140,740 | A | 10/2000 | Porat et al. |
| 6,171,850 | B1 | 1/2001 | Nagle et al. |
| 6,243,608 | B1 | 6/2001 | Pauly et al. |
| 6,334,859 | B1 | 1/2002 | Richter |
| 2002/0111658 | A1 | 8/2002 | Greenberg et al. |
| 2002/0188282 | A1 | 12/2002 | Greenberg |
| 2003/0069560 | A1 | 4/2003 | Adamis et al. |
| 2003/0176854 | A1 | 9/2003 | Rodstrom |

FOREIGN PATENT DOCUMENTS

| | | |
|---|---|---|
| WO | 93/03790 | 3/1993 |
| WO | 00/40089 | 7/2000 |
| WO | 01/12157 | 2/2001 |
| WO | 01/35928 | 5/2001 |
| WO | 01/37926 | 5/2001 |
| WO | 01/41736 | 6/2001 |
| WO | 01/64344 | 9/2001 |
| WO | 01/91902 | 12/2001 |

OTHER PUBLICATIONS

Barillaro, et al., Optical Materials, 17(1-2):91-94 (2001).

Bremus-Kobberling, et al., "Laser Microperforation of a Retina Implant," Presentation at Microtechnology Conference, Germany, Sep. 25-26, 2000.

Low, et al., "Microactuators Towards Microvalves for Responsive Controlled Drug Delivery," *Sensors & Actuators B* 67: 149-60 (2000).

Madou & Florkey, "From Batch to Continuous Manufacturing of Microbiomedical Devices," *Chem. Rev.*, 100: 2679-92 (2000).

Madou, *Fundamentals of Microfabrication*, pp. 468-512 (CRC Press 1997).

Madou & He, "Exploitation of a Novel Artificial Muscle for Controlled Drug Delivery," pp. 495-497 (1999).

Schwarz, et al., "Micro Implantable Visual Prostheses," 1st Annual Int'l IEEE-EMBS Special Topic Conference on Microtechnologies in Medicine & Biology, Lyon, France, Oct. 12-14, 2000.

Surbled, et al., "Shape Memory Alloys for Micromembranes Actuation," *SPIE*. 3825: 63-70 (1999).

Surbled, et al., "Array of Shape Memory Alloy One-Shot Micro-Valves for Drug Delivery," MME '99, Gif sur Yvette, France (Sep. 27-28, 1999).

Tierney, et al., "New Electrorelease Systems Based on Microporous Membranes," *J. Electrochem. Soc.*, 137:3789-3793 (1990).

Tierney, et al., "Electroreleasing Composite Membranes for Delivery of Insulin and Other Biomacromolecules," *J. Electrochem. Soc.*, 137:2005-06 (1990).

U.S. Appl. No. 09/638,109, filed Aug. 11, 2000, Santini, Jr., et al.

U.S. Appl. No. 09/715,493, filed Nov. 17, 2000, Santini, Jr., et al.

U.S. Appl. No. 09/727,858, filed Dec. 1, 2000, Richards, et al.

U.S. Appl. No. 09/798,562, filed Mar. 2, 2001, Santini, Jr., et al.

U.S. Appl. No. 09/975,672, filed Oct. 10, 2001, Sheppard, Jr., et al.

U.S. Appl. No. 09/975,786, filed Oct. 11, 2001, Sheppard, Jr., et al.

http://www.controldelivery.com/cdstech.htm (2001).

http://eyetechpharma.com/science/science_clinical.asp (2001).

* cited by examiner

FLEXIBLE MICROCHIP DEVICES FOR OPHTHALMIC AND OTHER APPLICATIONS

CROSS-REFERENCE TO RELATED APPLICATIONS

Priority is claimed under 35 U.S.C. § 119 to U.S. Ser. No. 60/260,725, filed Jan. 9, 2001.

BACKGROUND OF THE INVENTION

The present invention is generally in the field of implantable microchip devices and methods for use thereof, particularly in ophthalmic and other medical applications.

The relatively small size, rounded shape, and location of the eye have made the development of new methods and devices for drug delivery to the eye difficult. The most common method of drug delivery to the eye is by liquid eye drops. This method of drug delivery is limited to those drugs that can diffuse through the eye tissue (i.e. typically low molecular weight drugs) and those drugs that can be formulated as a liquid or gel.

Alternative delivery methods include the implantation of drug delivery devices inside of the eye. For example, U.S. Pat. No. 6,063,116 to Kelleher discloses an intraocular polymeric implant for sustained release of a cell proliferation-modulating agent. As another example, Ambati, et al, "Transscleral Delivery of Antibodies to the Posterior Segment" *Investigative Ophthalm. & Visual Sci.*, 40(4): 457-B417 (Mar. 15, 1999) discloses implanting osmotic pumps containing FITC-IgG on the scleral surface or beneath a lamellar scleral flap for targeted delivery to the choroid and retina.

These implants may allow larger molecular weight drugs to be delivered (depending on the presence of diffusion limitations based on the depth of the target tissue layer), but they typically only have the ability to passively release a single drug.

PCT WO 00/40089 discloses a method for delivering a therapeutic or diagnostic agent to the retina and choroid by contacting the sclera with the agent and using an implant device for enhancing transport of the agent through the sclera. The reference mentions that the implant can be a microchip comprising reservoirs containing the desired agent. It would be advantageous to develop new and improved systems using microchip devices, as described in U.S. Pat. No. 5,797,898, U.S. Pat. No. 6,123,861, PCT WO 01/64344, PCT WO 01/35928, and PCT WO 01/12157, for the controlled delivery of drugs and the controlled exposure of sensors in ophthalmic and other medical applications wherein implantation presents challenges such as described above for the eye.

It is therefore an object of the present invention to provide microchip devices for controlled release or exposure of reservoir contents at sites where known microchip devices may not be preferred, for example due to the size and/or location of the site.

It is another object of the present invention to provide microchip devices and methods of use thereof for delivery and sensing at locations in patients where implantation is desirable in small spaces, particularly those involving curved or rounded tissue surfaces.

It is a further object of the present invention to provide microchip devices and methods of use thereof for chemical and drug delivery to locations in and on the eye of patients in need thereof.

It is a further object of the present invention to provide microchip devices and methods of use thereof for the controlled exposure of reservoir contents, such as sensors, useful in the diagnosis and treatment of diseases and disorders of the eye.

SUMMARY OF THE INVENTION

Microchip device arrays that can conform to a curved surface are provided for the controlled release or exposure of reservoir contents. The arrays comprise two or more microchip device elements, each of which includes a plurality of reservoirs that contain molecules for controlled release or components for selective exposure, and a means for flexibly connecting the device elements.

Preferably, the means for flexibly connecting comprises a flexible supporting layer attached to a surface of the device elements. The flexible supporting layer can, for example, comprise a polymer, such as a polyimide, polyester, parylene, or hydrogel. The flexible supporting layer typically is attached the microchip device elements on the side distal the release/exposure opening of the reservoirs (i.e. the release side). Additionally or alternatively, the flexible supporting layer can be secured to the release side if the flexible supporting layer is provided with one or more apertures aligned the reservoir openings or if the flexible supporting layer is porous or permeable to (i) molecules releasable from the reservoirs or (ii) environmental molecules of interest that would need to contact the reservoir contents). Alternatively, the microchip device elements could be effectively imbedded within the flexible supporting layer.

In other embodiments, the means for flexibly connecting comprises one or more hinges or flexible tethers connecting two or more of the device elements.

In preferred embodiments, the microchip device array is suitable for implantation onto or into a patient, wherein the array can conform to the curvature of a tissue surface. In one embodiment, the array is implanted into or onto the eye of the patient, wherein the tissue surface comprises ophthalmic tissue.

In several embodiments, the reservoirs of the device elements contain drug molecules for release. In other embodiments, the reservoirs contain one or more secondary devices, such as a sensor, for exposure. A single array or a single device element can include both drugs for release and sensors. Such an array could be automated to release a particular dosage of drug in response to a condition or change measured by the sensors. The reservoirs also can contain diagnostic reagents, catalysts, combinatorial chemistry precursors, and fragrance molecules.

The microchip device array may comprise reservoir caps over the reservoirs, and optionally can include means for a user to wirelessly communicate with the microchip device elements. Such communicating means can comprise a photocell to receive incident light energy, such as from a laser source.

Microchip device array having active microchip device elements can comprise an energy storage means, such as a capacitor, a battery, or both. Optionally, the array includes electrical connections between two or more of the microchip device elements, such that the microchip device elements can be powered or controlled by a common energy source or control source, respectively.

Methods are provided for delivering drug molecules to a patient comprising implanting into or onto a tissue surface of the patient the microchip device array which contains drug, and selectively releasing from one or more of the reservoirs an effective amount of the drug molecules. In one embodiment, the microchip device array is implanted onto or into the sclera or another surface of the eye of the patient. The release of drug can be activated wirelessly, such as by application of light to the microchip device array. For example, an ophthalmic laser could be used. The laser light could, in one method, remove or permeate one or more reservoir caps which cover the reservoirs. Other suitable tissue surfaces include, but are not limited to, the stratum corneum or other skin tissues, mucosal membranes, blood vessels, bone, brain, and bladder.

In another method, molecules or a physical property is sensed at a site, wherein the method comprises implanting at a site the microchip device array which contains sensors, and selectively exposing at least one sensor of the sensors to molecules or a property at said site, thereby permitting said at least one sensor to sense said molecules or property. The sensor, for example, could comprise a pressure sensor or a chemical sensor.

More general methods are also provided for ophthalmic sensing.

Microchip devices have the advantage of small size, variable shape, and the ability to actively or passively control release or exposure of the contents of its reservoirs. The microchip devices can contain multiple drugs or chemicals, can contain sensors or diagnostic reagents, and can be controlled using microprocessors, remote control (i.e. telemetry), or biosensors. Additionally, the microchip devices for chemical delivery and selective exposure can be used with known ophthalmic technology (such as ophthalmic light sources, such as lasers or other focused light) to provide a source of power or data transmission, or as a means for opening reservoirs in the microchip devices, for example by triggering reservoir cap disintegration. The microchips can provide accurate and controlled local delivery of drugs, advantageously reducing or avoiding systemic release.

DETAILED DESCRIPTION OF THE INVENTION

The eye is a relatively small organ. Both the inside and outside surfaces of the eye are curved, so the size, shape, and rigidity of any device used to deliver drugs to the eye or used as a sensor in the eye is therefore important. Microchip devices can be made large or small, depending on the specific requirements of the particular application. The substrates for these microchips can be composed of semiconductors or other material that protects the contents of the reservoirs until it is desired to release them or expose them to the surrounding environment. For small devices, the shape and rigidity of the substrate material is not as important as it is for larger devices. Some typically rigid substrate materials (e.g., silicon) can be made flexible, for example, if they are made thin enough. However, as a flat, rigid microchip is enlarged or made thicker, it is less able to conform to the curvature of the eye. This can be a problem if it is necessary for the entire surface of the device to contact the surface of the eye, another curved tissue surface, or any other curved surface for that matter.

Figure 1A:
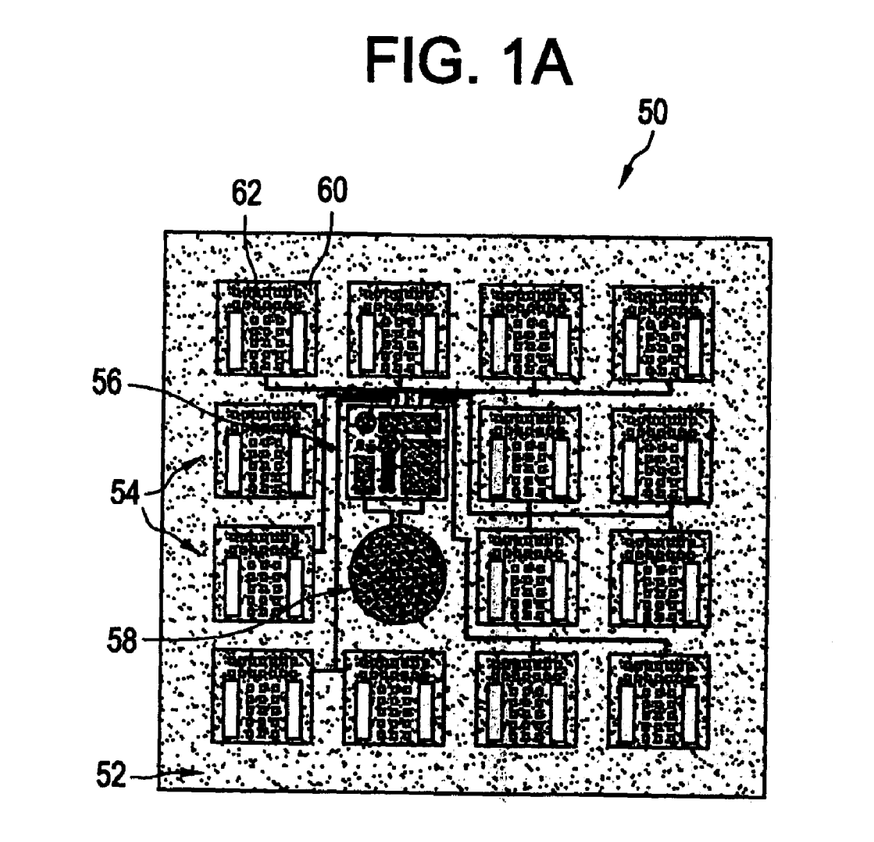
FIGS. 1A–C illustrate how an array of flat, rigid microchips are incorporated onto a flexible supporting layer containing electronic connections and shared power and control sources.
Figure 1B:
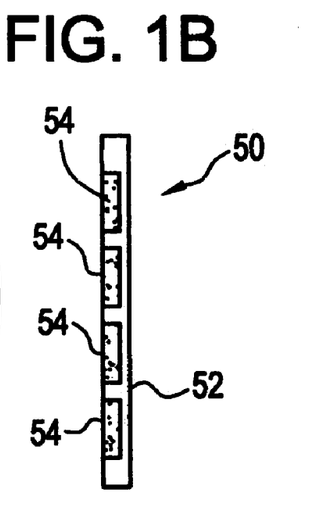
Figure 1C:
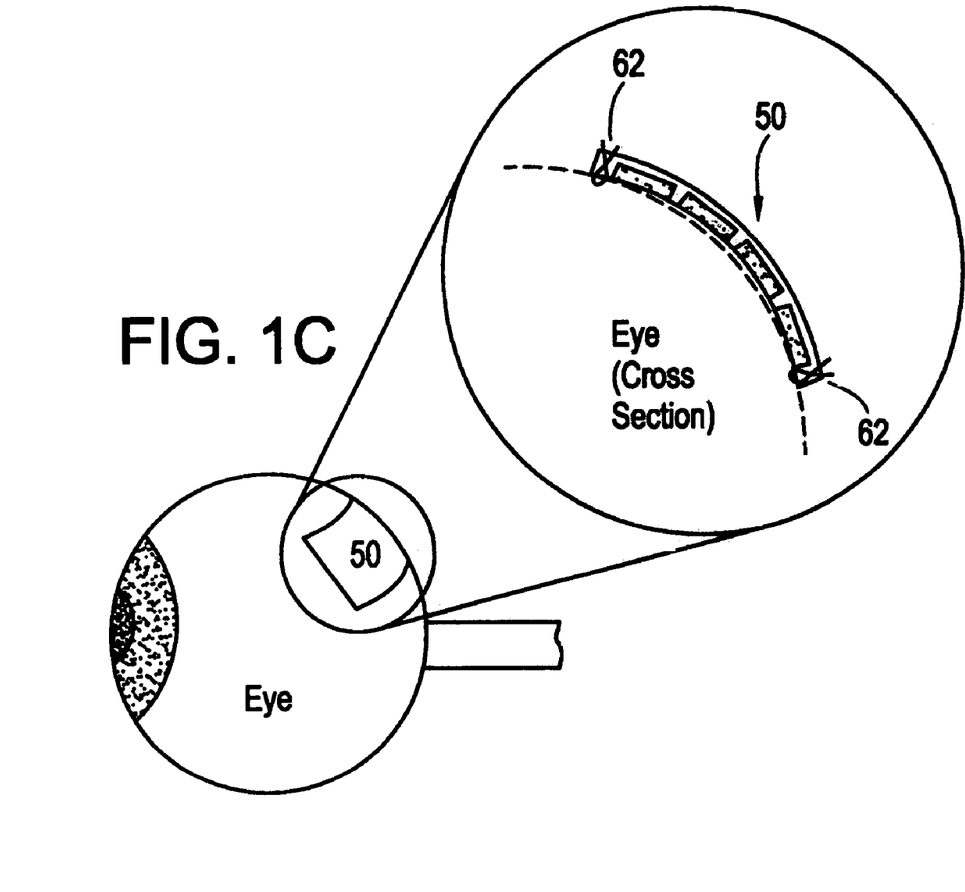

Therefore, microchip device arrays which can conform to curved surfaces, that is, flexible microchip devices, have been developed. In a preferred embodiment, this is accomplished with a microchip device that is made up of an array of several small microchip device elements that are attached to a flexible supporting layer. Each microchip on the supporting layer may be independently controlled (i.e. individual power and control sources) or the array of microchips may be controlled as one unit (i.e. shared power and control sources) through electrical connections built into the flexible supporting layer (see FIG. 1).

In preferred embodiments, the devices are adapted for use in delivering drugs or other chemicals to the eye, sensing changes in the eye or conducting other diagnostic tests, and combinations thereof, using, for example, a device array composed of rigid microchips which conforms to a curved surface of either the interior or exterior of the eye. Certain eye conditions, notably macular degeneration and diabetic retinopathy, can be treated with periodic administration of medication delivered to the eye; however, the means for doing so, such as injections, are difficult. An implanted microchip device, such as described herein, should provide an improved means for delivering doses of one or more types of medication to the eye on a periodic basis for an extended period of time. The microchips can provide accurate and controlled local delivery of drugs, advantageously reducing or avoiding systemic release.

The Devices

In preferred embodiments, the device comprises microchip device elements that are attached to or integral with a flexible supporting layer. Preferably, an array of at least two (e.g., at least four, at least five, at least twelve, etc.), microchip device elements forms a single, larger flexible device that can conform to the curvature of tissue surfaces, such as on surfaces of the eye, as detailed below.

In other embodiments, flexible microchip devices are provided in the form of a single microchip device element, or an array of two or more microchip device elements, having a flexible substrate. Such embodiments could be provided, for example, by molding or otherwise forming appropriate polymeric substrates, and would be particularly suitable for passive release designs.

The Microchip Device Elements

The microchip device (i.e. the microchip device elements) is described in U.S. Pat. No. 5,797,898 and No. 6,123,861, both to Santini, et al., and PCT WO 01/64344, WO 01/41736, WO 01/35928, and WO 01/12157, which are hereby incorporated by reference in their entirety. Each microchip device includes a substrate having a plurality of reservoirs containing reservoir contents for release or exposure.

In a preferred embodiment, each reservoir has a reservoir cap positioned on the reservoir over the reservoir contents, wherein release or exposure of the reservoir contents is controlled by diffusion through or disintegration of the reservoir cap. The reservoir cap can be an anode, such that upon application of an electric potential between a cathode and the anode the reservoir cap is oxidized to facilitate its disintegration, thereby exposing the reservoir contents to a surrounding fluid.

In another embodiment, the reservoir cap includes an electrically- or thermally-responsive polymer whose integrity or porosity can be modulated (i.e. increased or decreased) upon application of electrical energy to the reservoir cap (e.g., for the electrically responsive polymer) or to a nearby resistor or resistive heater (e.g., for the thermally responsive polymer). Similarly, the reservoir cap can include or be formed of a polymer having a porosity that can be modulated by application of electromagnetic energy, acoustic energy, or a particular chemical species (e.g., for chemical actuation) provided by the microchip device or other source.

The microchip devices can be made and assembled using microfabrication methods known in the art, particularly those methods described and referenced in U.S. Pat. No. 5,797,898 and No. 6,123,861, both to Santini, et al., and in PCT WO 01/64344, WO 01/41736, WO 01/35928, and WO 01/12157. These publications are hereby incorporated by reference.

The device is preferably constructed of, and/or coated with, materials known in the art to be physiologically acceptable for long-term implantation or contact with the ocular tissues.

Means for Flexibly Connecting

Preferably, the means for flexibly connecting comprises a flexible supporting layer secured to at least one surface of each of the device elements.

The flexible supporting layer typically is attached the microchip device elements on the side distal the release/exposure opening of the reservoirs (i.e. the release side). Additionally or alternatively, the flexible supporting layer can be secured to the release side if the flexible supporting layer is provided with one or more apertures aligned the reservoir openings or if the flexible supporting layer is porous or permeable to (i) molecules releasable from the reservoirs or (ii) environmental molecules of interest that would need to contact the reservoir contents). Alternatively, the microchip device elements effectively could be imbedded within the flexible supporting layer.

The flexible supporting layer can be made of essentially any flexible material, but preferably comprises a polymer. Representative examples of suitable polymers include polyimide, polyester, parylene, and hydrogels. Other flexible materials that are especially biocompatible include polyethylene, polypropylene and silicone.

The flexible supporting layer also could be a laminate structure. For example, it could be comprised of an inner flexible material containing electrical conductors that is coated with one or more biocompatible materials.

The microchip device elements, as well as other components, can be surface mounted onto or imbedded into the flexible supporting layer. For example, the microchip device elements and other components can be surface mounted using conductive adhesives, non-conducting adhesives (e.g., an epoxy), soldering, or wirebonding. Alternatively, the microchip elements could be mechanically attached, for example by screws or clips.

The flexible layer also may consist of or comprise a mesh material, which would generally be easier to suture to tissue. Such a mesh material could be biodegradable or non-biodegradable, depending upon the application.

In one embodiment, electrical connections or traces are built into the means for flexibly connecting the device elements. For example, the incorporation of electrical connections into flexible polymer films is well known by those skilled in the art of microelectronics packaging. Typical approaches include single and multiple layer flexible printed circuits, and Multichip Modules-Deposited (MCM-D) using organic (usually polyimide) dielectric layers. For example, in the "chips first" style of MCM-D, thinned chips are placed on a bottom dielectric layer and then interconnected layers are built up over them, thereby embedding the chips. Other chips, e.g., the microchip device elements can then be surface mounted. Flexible circuit and MCM-D fabrication techniques are described, for example, in Coombs, *Printed Circuits Handbook*, 4$^{th}$ ed. (McGraw-Hill 1996) and Harper, *Electronic Packaging and Interconnection Handbook*, 3$^{rd}$ ed. (McGraw-Hill 2000).

It is also understood that small, rigid, passive-release microchips also can be incorporated onto a supporting layer so that they can better conform to the curvature of the eye. Unlike the active microchips, the passive microchips do not require any power or control sources or electrical connections in the flexible substrate. In this case, the flexible substrate serves only to hold the passive microchip device elements in place.

In other embodiments, the means for flexibly connecting comprises one or more hinges or flexible tethers connecting two or more of the device elements, so that the array can conform to the curved surface. For example, each of the four edges of a square microchip device element could be connected by one or more hinges or flexible tethers to the edge of an adjacent microchip device element. The hinges or tethers could be connected at the corners or along the edges of the device elements. A flexible supporting layer could be used to form such tethers or hinges, or to complement them.

Contents of the Microchip Reservoirs

The microchip reservoir contents can be essentially any chemical or a secondary device, or portion thereof, that can be contained in a reservoir of the microchip device. The term "secondary device" typically refers to structures and does not include drugs or other chemical molecules that are intended to be released from the reservoirs. The microchip devices can contain multiple drugs or chemicals in a variety of forms (e.g., solid, liquid, or gel) and can contain sensors or diagnostic reagents.

In a preferred embodiment, the chemical is a therapeutic, prophylactic, or diagnostic agent. The term "drug" refers to any of these agents, unless a particular one is explicitly indicated. Representative types of suitable drugs include proteins, purified polypeptides and nucleic acid molecules, as well as synthetic and natural organic molecules.

Representative examples of suitable therapeutic or prophylactic molecules include antibiotics (e.g., tetracycline, chlortetracycline, bacitracin, neomycin, gentamicin, erythromycin, and penicillin); antibacterials such as sulfonamides, sulfadiazine, sulfacetamide, sulfamethizole and sulfisoxazole, nitrofurazone and sodium propionate; antivirals (e.g., idoxuridine, trifluorothymidine, acyclovir, gancyclovir and interferon); other anti-microbial drugs such as iodine-based preparation (e.g, triclosan, chlorhexidine); anti-allergenics (e.g., sodium cromoglycate, antazoline, methapyriline, chlorpheniramine); anti-inflammatories (e.g., hydrocortisone, hydrocortisone acetate, dexamethasone, dexamethasone 21-phosphate, fluorocinolone, medrysone, prednisolone acetate, fluoromethalone, betamethasone, and non-steroidal agents such as indomethacin, diclofenac, flurbiprofen, ibuprofen and acetylsalicylic acid); mydriatics (e.g., atropine sulfate, cyclopentolate, homatropine, scopolamine, tropicamide, eucatropine, and hydroxyamphetamine); sympathomimetics such as epinephrine; immunological drugs such as vaccines and immune stimulants; beta adrenergic blockers such as timolol maleate, levobunclol HCl and betaxolol HCl; growth factors such as epidermal growth factor and fibronectin; carbonic anhydrase inhibitors such as dichlorphenamide, acetazolamide and methazolamide and other drugs such as prostaglandins, antiprostaglandins, and prostaglandin precursors; angiogenesis inhibitors such as steroids, angiostatin, antiproliferative agents such as flurouracil and mitomycin; anti-angiogenic factors; immunomodulatory agents; vectors for gene transfer (e.g, DNA plasmids, viral vectors); cytotoxic agents, and chemotherapy medications.

Examples of diagnostic agents include imaging agents, such as contrast agents. The reservoir contents also can be selected from catalysts (e.g., zeolites, enzymes), non-therapeutic reagents, precursors for combinatorial chemistry, or combinations thereof, for example for use in diagnostic sensing and analytical biochemistry. The reservoir contents also could be non-biomedical molecules, such as fragrance molecules.

The reservoir contents also can include a secondary device, such as a sensor and sensing component. In a particularly preferred embodiment, the reservoirs contain pressure sensors, for example to measure intraocular pressure. The reservoir contents may either be released from or remain immobilized in the reservoir, depending on the particular application.

Types of sensors that can be contained within or provided near a reservoir include biosensors, chemical sensors, physical sensors, or optical sensors. Preferred sensors measure properties such as biological activity, chemical activity, pH, temperature, pressure, optical properties, radioactivity, and electrical conductivity. These may be discrete sensors (e.g., "off-the-shelf" sensors) or sensors integrated into the substrate. Biosensors typically include a recognition element such as an enzyme or antibody. The transducer used to convert the interaction between the analyte and recognition element into an electronic signal may be, for example, electrochemical, optical, piezoelectric, or thermal in nature. Representative examples of biosensors constructed using microfabrication methods are described in U.S. Pat. No. 5,200,051, No. 5,466,575, No. 5,837,446, and No. 5,466,575.

There are several different options for receiving and analyzing data obtained with the secondary devices located in the microchip devices. First, the output signal from the device can be recorded and stored in writeable computer memory chips. Second, the output signal from the device can be directed to a microprocessor for immediate analysis and processing. Third, the signal can be sent to a remote location away from the microchip. For example, a microchip can be integrated with a radio transmitter in order to transmit a signal (e.g., data) from the microchip to a computer or other remote receiver source. The microchip can also be controlled using the same transmission mechanism. Power can be supplied to the microchip locally by a microbattery or remotely by wireless transmission. Ophthalmic lasers can be used to wirelessly transmit power and data, as described in detail below.

Individual reservoirs may contain multiple types of chemicals, multiple types of devices, or combinations of devices and chemicals. In various embodiments, the microchip devices may include one or more drugs, one or more sensors, or combinations thereof.

Interface with the Eye or other Implantation Sites

The microchip devices described herein are useful at a variety of site in which a single, larger, rigid microchip device may not be preferred. Examples of such sites include, but are not limited to, implantation sites in humans and other mammals. As used herein, "implantation" and "implanting" typically refer to securely positioning a microchip device onto a tissue surface. For example, the microchip devices described herein can be attached to an outer surface of the eye or implanted within the eye using or adapting known medical and surgical techniques.

Alternatively, the device is designed to conform to another curved tissue surface, such as the skin, mucosal tissue surfaces, blood vessel walls (interior or exterior side), the stratum corneum or other skin tissues, mucosal membranes, blood vessels, bone (e.g., the skull, the femur), brain, and other organs tissue surfaces, such as the bladder. Such devices can be used for drug delivery and sensing applications. The flexible devices also may serve to reposition the contacted tissue for therapeutic purposes, such as to mechanically maintain the patency of a tissue lumen, for example, while releasing anti-coagulants or anti-atherosclerotic agents. In the bladder, the flexible device could be used, for example, to deliver bacillus Calmette-Guerin (BCG) to the interior surface for the treatment of superficial bladder cancer.

Power and Data Transmission

The active microchip devices require power to initiate release of molecules from the reservoirs or exposure of reservoir contents. There are two primary methods of supplying power to initiate release or exposure from active microchip devices. These include the use of pre-charged power sources and the use of on-demand power sources. Pre-charged power sources (e.g., pre-charged micro-batteries) can be integrated with the microchip and its associated electronics. Such a pre-charged micro-battery can be, for example, a thin film battery fabricated on the microchip itself, or it can exist as a separate component that is connected to the microchip through interconnects and packaging. In the case of pre-charged power sources, the power source must store all the power required during the operating lifetime of the microchip. If it cannot store all of the required power, then a new battery at some point must replace the old battery during the life of the microchip.

On-demand power sources (e.g., wireless transmission and reception of power) do not require a power storage unit to be physically connected to or included with the microchip, because the necessary power can be transmitted to the microchip at any time. Unlike pre-charged power sources, microchip systems with the capability to receive power by wireless methods do not need to store all of the power required for the operating life of the microchip. Instead, power can be applied to the microchip on demand (i.e. when needed). However, microchips relying on on-demand power sources can include a "re-chargeable" power storage unit (i.e. capacitor, re-chargeable micro-battery), if it is desired to store small amounts of power on or near the microchip. The distinction is that pre-charged power sources must contain all the required power or be replaced, and on-demand power sources do not have to contain all the required power because they can receive power or be re-charged at any time. On-demand power by wireless transmission is known, and is described for example in U.S. Pat. No. 6,047,214 to Mueller, et al.; U.S. Pat. No. 5,841,122 to Kirchhoff; and U.S. Pat. No. 5,807,397 to Barreras. The basic elements of a system for the wireless transmission of power to a microchip for chemical release or selective exposure of reservoir contents include a transmitter to deliver power by means of electromagnetic waves (i.e. radio frequency signal generator or RF), light (e.g., ophthalmic laser) or ultrasound, and a receiver. Additional components may include a means of power conversion such as a rectifier, a transducer, a power storage unit such as a battery or capacitor, and an electric potential/current controller (i.e. potentiostat/galvanostat).

Each of these units (except for the external energy transmission source) may be fabricated on the microchip ("on-chip" components) using MEMS fabrication techniques as described, for example, in Madou, *Fundamental of Microfabrication* (CRC Press, 1997) or using standard microelectronics processing techniques as described, for example, in Wolf & Tauber, *Silicon Processing for the VLSI Era* (Lattice Press, 1986). In addition, each of these units (except the external energy transmission source) may exist as "off the shelf" microelectronic components that can be connected to the microchips using hybrid electronic packaging or multichip modules (MCMs). An active microchip with the capability of receiving power through wireless means also can be composed of a combination of "on-chip" components and "off the shelf" components. Methods for sending and receiving data using wireless technology are very similar to those used for the wireless transmission of power. Therefore, the design and fabrication of such wireless power and data transmission systems are known or can be made using no more than routine experimentation by those skilled in the art.

Ophthalmic Embodiments

In one embodiment, the ophthalmic microchip device is in the form of an array of small, rigid, drug-containing microchips that are attached to a flexible supporting layer so that the entire array can conform to the outer surface of the back of the eye. The microchips are connected to each other by flexible electrical connections incorporated into the supporting layer. In this embodiment, the array of microchips is controlled by a single microprocessor and power is supplied by a small battery. The array is attached to the back surface of the eye and is held in place by several small sutures through the supporting layer and into the outer tissue of the eye. The microprocessor is preprogrammed to release drug from specific reservoirs by directing power from the battery to specific reservoir caps through multiplexing circuitry. In a specific embodiment, the caps are made of gold and they disintegrate in biological solutions when electric potentials of approximately 1 volt (vs. SCE) are applied to them. Once the drug is released from a reservoir, it is in contact with the surface of the eye and diffuses into the eye. This process can be repeated numerous times with several different drugs being released from a single microchip or array of microchips. The type and configuration of device components and the number of microchips in the array can be varied as needed for particular applications.

This embodiment is illustrated in FIGS. 1A–C. FIGS. 1A and 1B show, in plan and cross-sectional views, respectively, an ophthalmic microchip device 50, which includes microchip device elements 54 attached to flexible supporting material 52. In this active-release embodiment, the device 50 also includes active electronics 56 (e.g., microprocessors, multiplexers, timers, etc.) and a microbattery 58. Each microchip device element 54 includes substrate 60 containing a plurality of reservoirs 62. The reservoirs can contain drugs or other reservoir contents as described herein. FIG. 1C illustrates how the device 50 could be implanted onto the surface of the eye. The cross-sectional view of the eye (wherein the surface of the eye is represented by a curved, dashed line) onto which device 50 is mounted with sutures 62. Other techniques known in the art also could be used to secure the device as appropriate.

Methods of Using the Devices

The microchip device elements can be used and operated generally as described in U.S. Pat. No. 5,797,898, U.S. Pat. No. 6,123,861, PCT WO 01/64344, PCT WO 01/35928, and PCT WO 01/12157, and as described herein.

As described herein, reservoir activation can be conducted wirelessly. Generally, this refers to telemetry (i.e. the transmitting and receiving) accomplished using a first coil to inductively couple electromagnetic energy to a matching/corresponding second coil. The means of doing this are well established, with various modulation schemes such as amplitude or frequency modulation used to transmit the data on a carrier frequency. The choice of the carrier frequency and modulation scheme will depend on the location of the device and the bandwidth required, among other factors. Other data telemetry means also may be used. Examples include optical communication, where the receiver is in the form of a photocell, photodiode, and/or phototransistor, and where the transmitter a light-emitting diode (LED) or laser.

Light Actuation of Microchip Devices

The power requirements for electrochemically actuated silicon microchip devices with thin film gold reservoir caps are sufficiently small that this power can be supplied optically. An ophthalmic laser can be used to both supply the power and communicate instructions to the device, as is done in many wireless systems where the signal carrying power is modulated to contain information to be communicated to the device. Alternatively, focused light from a non-laser source can be sufficient to operate the device.

In a preferred embodiment, focused light, such as from a laser source, is used to activate or actuate the reservoirs of microchip devices following implantation of the device. For example, lasers are used routinely in eye surgeries and other eye procedures for the treatment of conditions such as diabetic retinopathy, retinal detachments, and age-related macular degeneration. Many of these procedures are simple, outpatient procedures carried out in an ophthalmologist's office. The microchip devices can be implanted into the eye and then activated using such lasers to transmit power, data or both for powering and controlling the device. An ophthalmologist can initiate drug release and communication with eye-implanted microchips by directing an ophthalmic laser toward the appropriate portion of the microchip in (or on) the patient's eye for those locations (i.e. implantation sites) where the microchip device is readily accessible. Many ophthalmologists are already skilled in the use of such lasers.

In a preferred embodiment, the implanted wireless ocular delivery system includes the drug-containing microchip, controller, external interface(s), power conversion electronics, and actuation electronics. The external interface and power conversion electronics typically consists of a photocell to receive the incident light (e.g., laser) energy, circuitry to generate the needed voltage(s), storage means such as a capacitor or battery, and circuitry to decode information transmitted by modulating the laser input. The controller typically is a microprocessor, memory, clock, though a dedicated integrated circuit may be useful for some applications.

Electronics required to actuate electrochemical microchips includes means for controlling the electrode potential, such as a potentiostat/galvanostat, and a demultiplexer to direct the potential to the desired reservoir(s). If desired, the system can provide feedback, for example, to confirm the successful delivery of a dose. This information can be transmitted back to the operator or to a computer monitoring system optically using a light-emitting diode (LED) or by other modes of wireless transmission (e.g., RF).

Wireless Reservoir Activation

Ophthalmic lasers also can be used to open the reservoirs of microchip devices implanted inside the eye or attached to the outside of the eye. The physician can direct the laser to one or more reservoir caps, causing the cap material to disintegrate or become permeable, thereby releasing the drugs or chemicals contained in the reservoir or exposing other reservoir contents (e.g., sensors) of the reservoir to the surrounding environment. For example, the reservoir cap is made of a low melting temperature polymer and the reservoir is opened when the laser softens or melts the reservoir cap.

In one embodiment, a microchip device having polymeric reservoir caps is implanted into the interior of the eye and held in place with sutures. The polymer caps do not dissolve or allow the drug to be released into the eye without the application of an external stimulus. In this embodiment, an ophthalmic laser is directed at one or more polymeric reservoir caps when release is desired from the corresponding reservoirs. The ophthalmic laser creates a local increase in temperature that causes the polymeric reservoir cap to soften and melt. The drug inside that reservoir then diffuses out of the reservoir and into the intraocular fluid. This implanted device can be used, for example, to deliver drug as needed over an extended period of time. For example, the patient can visit the physician periodically, e.g., every two to four weeks, and the physician uses an ophthalmic laser to open one reservoir (or several of them) of the implanted microchip device to release drugs into the patient's eye.

In a similar embodiment, the physician uses the ophthalmic laser to open a reservoir that contains one or more sensors, which can be exposed by the physician when desired. Representative sensors included pressure sensors, chemical sensors, and immunological sensors. A chemical sensor, such as an oxygen electrode, is one example of a useful sensor. Another example is a pressure sensor, which can be used to help monitor the progression of some eye diseases, such as glaucoma, by measuring and recording pressure changes in the eye. The pressure sensing function can be related to the release of drug from another reservoir, so that, for example, upon detection of an abnormally high intraocular pressure, the microchip device signals the release of a pressure reducing drug from another microchip reservoir, which can be in the same device or in separately fabricated device that is in communication with the pressure sensing microchip device.

An implantable wireless ocular delivery system would typically include (1) the microchip device (containing one or more drugs and/or sensors) with its local controller, external interfaces, power conversion electronics, and actuation electronics; and (2) the focused light source. The external interface and power conversion electronics typically would include a photocell to receive the incident light energy, circuitry to generate the needed voltage, storage means such as a capacitor or battery, and circuitry to decode information transmitted by modulating the laser input. The controller typically would be a microprocessor with associated support circuitry such as a memory and a clock, although a dedicated integrated circuit may work for some embodiments. Electronics required to actuate electrochemical microchips typically would include means for controlling the electrode potential, such as a potentiostat or galvanostat, and a demultiplexer to direct the potential to the desired reservoir. If desired, the system would provide feedback, for example, to confirm the successful delivery of a dose. This information could be transmitted back to the operator or to a computer monitoring system, either optically by using a light-emitting diode (LED) or by other modes of wireless transmission, such as RF.

Figure 2A:
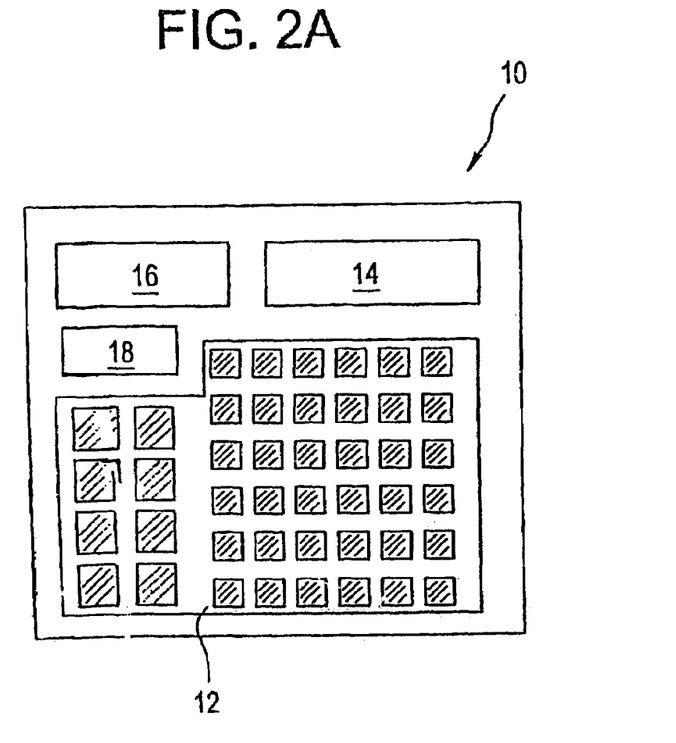
FIG. 2A illustrates one embodiment of a configuration of an ophthalmic microchip device for drug release into the eye that is equipped for power and data transmittal by laser.

FIG. 2A illustrates one possible configuration of the microchip device configuration, wherein microchip device 10 includes an array of reservoirs 12 containing drug to be released or sensor to be exposed, power conversion, actuation electronics and local controller area 14, photocell 16, LED or wireless telemetry transmitter 18.

Figure 2B:
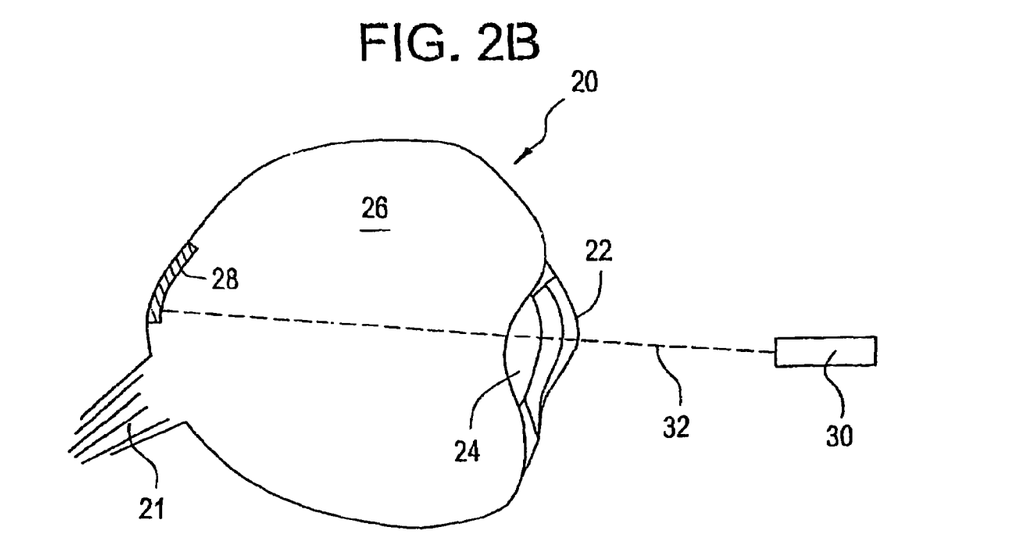
FIG. 2B illustrates a process of using an ophthalmic laser to transmit power and data to such an ophthalmic microchip device implanted in the eye.

An ophthalmologist could initiate drug release and communication with eye-implanted microchip device by directing an ophthalmic laser toward the appropriate portion of the implanted microchip in the patient's eye. See FIG. 2B, which illustrates an eye 20 with optic nerve 21, wherein microchip device 28 is implanted at the back of the interior of the eye. An ophthalmic laser 30 directs power and data via laser light 32 through cornea 22, lens 24, and vitreous humor 26, to power and communicate with the implanted microchip device 28. Many ophthalmologists are already skilled in the use of such lasers, so these procedures could be readily performed.

Applications of the Ophthalmic Microchip Devices

The microchip devices and methods of use can be used for a variety of therapeutic, prophylactic, and diagnostic ophthalmic applications, as well as other (non-ophthalmic) medical implant application.

In a preferred embodiment, the devices are used in the treatment of retinal or choroidal diseases, such as macular degeneration, glaucoma, diabetic retinopathy, retinitis pigmentosa, retinal vein occlusions, sickle cell retinopathy, choroidal neovascularization, retinal neovascularization, retinal edema or ischemia.

In some applications, the devices are used in the control of inappropriate proliferation of cells on or within the eye. The specific type and location of the cells depends upon the particular disease or disorder. Examples of types of inappropriate cell proliferation include cancerous malignancies, wherein the cell is a cancer cell, scarring, wherein the cell is a normal fibroblast, and diseases wherein the proliferating cell is an epithelial cell, such as a lens epithelial cell, which can impair vision. One specific application is the inhibition of wound healing at the site of implantation of a filtering bleb or fistula to create a drainage channel for aqueous humor outflow to lower elevated intraocular pressure, which is associated with glaucoma.

Other Applications of the Microchip Sevice Arrays

The devices described herein have a wide variety of both medical and non-medical uses. For example, other medical applications for the microchip devices include drug delivery and sensing at sites such as the wall (interior or exterior side) of a blood vessel and on or within other organs such as the bladder. Other tissue surfaces (i.e. implantation sites) include skin (e.g., the stratum corneum, for example, where the microchip device could be used for transdermal drug delivery) and mucosal tissue surfaces (e.g., for vaginal or buccal drug delivery), blood vessel walls (interior or exterior side), and other organs, such as the bladder.

Representative non-medical uses include industrial diagnostics, chemical research, consumer products (e.g., fragrance release), etc.

Modifications and variations of the methods and devices described herein will be obvious to those skilled in the art from the foregoing detailed description. Such modifications and variations are intended to come within the scope of the appended claims.

We claim:

1. A microchip device array for the controlled release or exposure of reservoir contents comprising:
   two or more microchip device elements, each of which includes a plurality of reservoirs which contain molecules for controlled release or components for selective exposure; and
   a means for flexibly connecting said device elements, so as to form a flexible array which can conform to a curved surface.

2. The microchip device array of claim 1, wherein the means for flexibly connecting comprises a flexible supporting layer attached to a surface of the device elements.

3. The microchip device array of claim 2, wherein the flexible supporting layer comprises a polymer.

4. The microchip device array of claim 3, wherein the polymer is selected from the group consisting of polyimides, polyesters, parylenes, and hydrogels.

5. The microchip device array of claim 2, wherein the flexible supporting layer is porous or permeable to molecules releasable from the reservoirs or provided with one or more apertures through said flexible supporting layer.

6. The microchip device array of claim 1, wherein the means for flexibly connecting comprises one or more hinges or flexible tethers connecting two or more of the device elements.

7. The microchip device array of claim 1 for implantation onto or into a patient, wherein the array can conform to the curvature of a tissue surface.

8. The microchip device array of claim 7 for implantation into or onto the eye of the patient, wherein the tissue surface comprises ophthalmic tissue.

9. The microchip device array of claim 7, wherein the tissue surface is selected from the group consisting of the stratum corneum, mucosal membranes, blood vessels, bone, brain, and bladder.

10. The microchip device array of claim 1, wherein the microchip device elements further comprise a plurality of discrete reservoir caps over the molecules in the reservoirs, wherein each reservoir cap controls release of the molecules from one of the reservoirs.

11. The microchip device array of claim 1 further comprising a means for wirelessly communicating with the microchip device elements.

12. The microchip device array of claim 11, wherein the communicating means comprises a photocell to receive incident light energy.

13. The microchip device array of claim 1 further comprising an energy storage means.

14. The microchip device array of claim 13, wherein the energy storage means comprises a capacitor, a battery, or both.

15. The microchip device array of claim 1 further comprising electrical connections between two or more of the microchip device elements, such that the microchip device elements can be powered or controlled by a common energy source or control source, respectively.

16. The microchip device array of claim 1, wherein the reservoirs contain drug molecules.

17. The microchip device array of claim 1, wherein the reservoirs contains one or more secondary devices for exposure.

18. The microchip device array of claim 17, wherein the secondary device comprises a sensor.

19. The microchip device array of claim 18, wherein the sensor is a pressure sensor or a chemical sensor.

20. The microchip device array of claim 1, wherein the microchip device elements comprise reservoirs which contain drug molecules and at least one reservoir which contains a sensor.

21. The microchip device array of claim 1, wherein the reservoirs contain molecules selected from the group consisting of diagnostic reagents, catalysts, combinatorial chemistry precursors, and fragrance molecules.

22. The microchip device array of claim 1, wherein the electrical traces are built into the means for flexibly connecting said device elements.

23. The microchip device array of claim 1, which comprises flexible, passive release device elements.

24. The microchip device array of claim 7, which enhances the patency of a tissue lumen or other organ structure in the patient.

* * * * *